United States Patent [19]

Ploog

[11] Patent Number: 4,983,778

[45] Date of Patent: Jan. 8, 1991

[54] ALKOXYLATION PROCESS USING A CATALYST COMPOSITION CONTAINING ESTERS OF TITANIC ACID AND ZIRCONIC ACID

[75] Inventor: Uwe Ploog, Haan, Fed. Rep. of Germany

[73] Assignee: Henkel Kommanditgesellschaft auf Aktien, Duesseldorf, Fed. Rep. of Germany

[21] Appl. No.: 346,037

[22] Filed: May 2, 1989

[30] Foreign Application Priority Data

May 2, 1988 [DE] Fed. Rep. of Germany ....... 3814849

[51] Int. Cl.$^5$ .............................................. C07C 41/03
[52] U.S. Cl. .................................. 568/618; 564/475; 260/410.6
[58] Field of Search ........................ 568/618; 564/475; 260/410.6

[56] References Cited

U.S. PATENT DOCUMENTS 4,727,199  2/1988  King ..................................... 568/608

FOREIGN PATENT DOCUMENTS

| | | |
|---|---|---|
| 092256 | 4/1982 | European Pat. Off. . |
| 082569 | 12/1982 | European Pat. Off. . |
| 085167 | 12/1982 | European Pat. Off. . |
| 091146 | 3/1983 | European Pat. Off. . |
| 115083 | 12/1983 | European Pat. Off. . |
| 228121 | 7/1987 | European Pat. Off. . |
| 632953 | 2/1977 | Fed. Rep. of Germany . |

OTHER PUBLICATIONS

JAOCS, vol. 63, 691–695 (1986).
HAPPI, 52–54 (May 1986).

*Primary Examiner*—Howard T. Mars
*Attorney, Agent, or Firm*—Ernest G. Szoke; Wayne C. Jaeschke; Daniel S. Ortiz

[57] ABSTRACT

Alkoxylation products of organic compounds containing active H atoms with a narrow homolog distribution range is produced by using as a catalyst in the alkoxylation process a catalyst composition comprising:

a. Esters of titanic and/or zirconic acid with monoalkanols containing 1 to 4 carbon atoms in combination with, b. sulfuric acid and/or alkanesulfonic acid containing 1 to 6 carbon atoms and/or hydroxyarylsulfonic acids as catalysts for the ethoxylation or propoxylation of compounds containing active H atoms provide the alkoxylation products with a narrow homolog distribution range.

3 Claims, No Drawings

ALKOXYLATION PROCESS USING A CATALYST COMPOSITION CONTAINING ESTERS OF TITANIC ACID AND ZIRCONIC ACID

BACKGROUND OF THE INVENTION

1. Field of the Invention

This invention is a process for the ethoxylation or propoxylation of compounds containing active H atoms. In particular, the invention is a process using a catalyst system comprising esters of titanic acid and/or zirconic acid.

In the context of the invention, useful compounds containing active H atoms, upon alkoxylation form surfactants. Useful compounds include fatty alcohols, Guerbet alcohols, fatty acids and fatty amines which, on ethoxylation or propoxylation, form nonionic surfactants. A typical example is the reaction of fatty alcohols containing 10 to 18 carbon atoms with several mols of ethylene oxide and/or propylene oxide in the presence of a catalyst.

2. Description of Related Art

The polyalkoxylation reaction has been carried out using catalysts such as calcium and strontium hydroxides, alkoxides and phenoxides (EP-A No. 00 92 256), calcium alkoxides (EP-A No. 00 91 146), barium hydroxide (EP-B No. 0 115 083), basic magnesium compounds, for example alkoxides (EP-A No. 00 82 569), magnesium and calcium fatty acid salts (EP-A No. 0 85 167), antimony pentachloride (DE-A No. 26 32 953), aluminium isopropylate/sulfuric acid (EP-A No. 22 81 21).

Other typical polyalkoxylation catalysts are potassium hydroxide and sodium methylate.

The known catalysts have the disadvantage that they are difficult to incorporate into the reaction system and/or are difficult to produce. In addition, where alkali hydroxides and alkali alcoholates are used, the range of the degree of polyalkoxylation, i.e. the homolog distribution, which will be discussed in more detail hereinafter, is broad. Although acidic catalysts, for example antimony pentachloride, bring about a narrower homolog distribution and a lower fatty alcohol content of the reaction products, they are highly corrosive and, in some cases, toxic. Although, where mixtures of aluminium alcoholates and sulfuric acid are used, it is possible to obtain a narrow homolog distribution in the alkoxylation products for high conversion levels in the case of linear fatty alcohols, the same does not apply to branched alcohols, for example, Guerbet alcohols.

A narrow range of the degree of polyalkoxylation is particularly important for fatty alcohol polyalkoxylates, cf. JAOCS, Vol. 63, 691–695 (1986), and HAPPI, 52–54 (1986). Accordingly, the alkoxylates having a narrow range of homolog distribution, have the following advantages:

low pour points, relatively high smoke points, require fewer mols alkoxide to achieve solubility in water, require lower quantities of hydrotropes to achieve compatability with liquid universal detergents, have a relatively faint odor due to the presence of free (unreacted) fatty alcohols reduces pluming in the spray-drying of detergent slurries containing fatty alcohol polyalkoxylate surfactants.

The homolog distribution of fatty alcohol polyalkoxylates is related to the type of catalyst used. A measure of the homolog distribution is the Q value according to the following relation:

$$Q = n^* \cdot p^2$$

in which n* is the average number of adducts (averge degree of ethoxylation) and p is the percentage of adduct ethoxylated to a certain degree, which is predominantly formed. Accordingly, a high Q value signifies a narrow homolog distribution range.

Ethoxylates having a low content of free fatty alcohols have an increased conversion level in the production of ether carboxylic acids by reaction of the ethoxylates with sodium chloroacetates in the presence of alkali hydroxides. In addition, narrow-range ethoxylates are extremely effective thickeners for surfactant solutions.

BRIEF DESCRIPTION OF THE INVENTION

Other than in the operating examples, or where otherwise indicated, all numbers expressing quantities of ingredients or reaction conditions used herein are to be understood as modified in all instances by the term "about."

It has now been discovered that, by using esters of titanic and/or zirconic acid with monoalkanols containing 1 to 4 carbon atoms together with sulfuric acid and/or alkanesulfonic acids containing 1 to 6 carbon atoms and/or hydroxyarylsulfonic acids as catalysts for the ethoxylation or propoxylation of compounds containing active H atoms, it is possible to obtain a narrow homolog distribution in the polyalkoxylation products, the content of free fatty alcohols in the reaction products being distinctly reduced by comparison with conventional catalysts. In addition, branched fatty alcohols, such as the Guerbet alcohols can be polyalkoxylated without difficulty.

DETAILED DESCRIPTION OF THE INVENTION

The titanic and/or zirconic acid esters with monoalkanols containing 1 to 4 carbon atoms useful in the practice of the invention are known and commercially available compounds; typical examples are titanium tetramethylate, tetraethylate, tetra n-propylate, tetra i-propylate and tetra i-butylate and the corresponding zirconic acid esters.

According to the invention, the esters of titanic and/or zirconic acid with monoalkanols containing 1 to 4 carbon atoms are used in admixture with sulfuric acid and/or alkane sulfonic acids containing 1 to 6 carbon atoms and/or aryloxysulfonic acids. Neither the titanic acid and/or zirconic acid esters nor sulfuric acid nor the sulfonic acids alone are effective as a catalyst in practical concentrations. The desired catalytic effect only occurs when these components are suitably combined. Suitable alkanesulfonic acids containing 1 to 6 carbon atoms are, for example, methane, ethane, propane, butane, pentane and hexanesulfonic acids. Phenolsulfonic acid is a typical example of an equally suitable hydroxyarylsulfonic acid.

In one preferred embodiment of the process of the invention, the catalyst composition is used in a quantity of from 0.2 to 2% by weight, based on the end product of the ethoxylation or propoxylation reaction.

In another preferred embodiment of the invention, the esters of titanic and/or zirconic acid and sulfuric acid and/or alkanesulfonic acids containing 1 to 6 carbon atoms and/or hydroxyarylsulfonic acids are used in molar ratios of from 1:1 to 1:4.

The invention is illustrated by the following Examples.

1. Preparation of the catalysts

The catalyst compositions are best prepared by mixing the quantities shown in Table 1 with the material to be polyalkoxylated, particularly the fatty alcohols according to Table 1. However, the catalyst can be used, for example, in the form of a concentrated alcoholic solution of which aliquots are used.

2. Alkoxylation conditions

The catalyst compositions were added to the fatty alcohols to be alkoxylated as listed in Table 1 and transferred to a suitable autoclave. After evacuation for about 30 minutes at 100° C. and purging with nitrogen, the temperature was increased to about 180° C. and the desired quantity of ethylene oxide was introduced under a maximum pressure of 5 bar. After a reaction time of 30 minutes, unreacted alkylene oxide was separated off at 100° C./14 mbar.

The OH number and polyglycol (PG) content of the alkoxylates formed were determined. A gas chromatogram was also taken to determine the homolog distribution or the Q value on the basis of the percentage areas measured.

EXAMPLES 1 to 6

In these Examples, the above procedure was adopted for the ethoxylation of fatty alcohols with 2 mol ethylene oxide. Table 1 shows the fatty alcohols and catalysts used, the quantity of catalyst used (in mmol/100 g ethoxylation product), the reaction time, the reaction temperature, the Q value determined, the OH number of the ethoxylation products (actual/calculated), the content of free fatty alcohols (FFA, %) and the polyglycol content (PG, %).

COMPARISON EXAMPLES

The results obtained with catalysts known from the prior art are shown in Table 2.

The fatty alcohols mentioned in the Tables were commercially available, technical fatty alcohol mixtures having the following composition:

$C_{12-14}$: fatty alcohol having the following chain length distribution: 0–2% $C_{10}$, 70–75% $C_{12}$, 20–30% $C_{14}$, 0–2% $C_{16}$; iodine value below 0.3, average molecular weight 194, hydroxyl number 285–293.

$C_{12}$: fatty alcohol having the following chain length distribution: 0–2% $C_{10}$, at least 97% $C_{12}$, 0–3% $C_{14}$, iodine value below 0.3, average molecular weight 188, hydroxyl number 295–301.

Guerbet $C_{16}$: 2-hexyldecanol having a hydroxyl number of 190 to 230, an iodine value below 10 and a viscosity at 20° C. of approximately 40 mPa.s.

TABLE 1

Ethoxylation of alcohols with 2 mol ethylene oxide

| Example no. | Alcohol | Catalyst | Quant. of cat. (mmol/100 g product) | Reaction time (hrs.)/ temp. (°C.) | Q | OH number Actual/Calc. | FFA (%) | PG (%) |
|---|---|---|---|---|---|---|---|---|
| 1 | $C_{12-14}$ | $Ti(OiC_3H_7)_4$/ $H_2SO_4$ | 2.7 / 5.7 | 5/180 | 2258 | 220/204 | 16 | 1.2 |
| 2 | $C_{12}$ | $Ti(OiC_3H_7)_4$/ $HO-C_6H_4-SO_3H$ | 5 / 10 | 5.5/150 | 2436 | 232/204 | 16.7 | 1.6 |
| 3 | $C_{12}$ | $Ti(OiC_3H_7)_4$/ $H_2SO_4$ | 4.4 / 2.2 | 8/140 | 1700 | 218/204 | 12.5 | 2.7 |
| 4 | $C_{12}$ | $Zr(OiC_3H_7)_4$/ $CH_3SO_3H$ | 5 / 10 | 4/140 | 1682 | 216/2104 | 9.8 | 0.3 |
| 5 | Guerbet $C_{16}$ | $Ti(OiC_3H_7)_4$/ $CH_3SO_3H$ | 4.5 / 9.1 | 7/180 | 899 | 147/155 | 17.9 | 10 |
| 6 | Guerbet $C_{16}$ | $Ti(OiC_3H_7)_4$/ $CH_3SO_3H$ | 9.0 / 18.2 | 3/180 | 924 | 163/155 | 20.4 | n.b. |

TABLE 2

Ethoxylation of alcohols with 2 mols ethylene oxide (Comparison Tests)

| Fatty alcohol | Catalyst | Quant. of cat. (mmol/100 g product) | Reaction time (hrs.)/ temp. (°C.) | Q | OH number Actual/Calc. | FFA (%) | PG (%) |
|---|---|---|---|---|---|---|---|
| $C_{12-14}$ | $NaOCH_3$ | 2 | 1/180 | 655 | 204/204 | 31.9 | 0.3 |
| Guerbet $C_{16}$ | $NaOCH_3$ | 2 | 3/180 | 225 | 164/155 | 40.2 | 4.1 |
| $C_{12}$ | $SbCl_5$ | 1.7 | 5/180 | 1972 | 208/204 | 8.3 | 1.2 |
| $C_{12}$ | $Al(OiC_3H_7)_3$/ $H_2SO_4$ | 4.4 / 4.4 | 2.5/140 | 3330 | 216/204 | 16 | 4.6 |
| Guerbet $C_{16}$ | $Al(OiC_3H_7)_3$/ $H_2SO_4$ | 4.9 / 2.5 | 3/140 | 880 | 178/155 | 49 | 11.3 |

What is claimed is:

1. In a process wherein compounds containing active H atoms are reacted with ethylene oxide, propylene oxide, or mixtures thereof, at an elevated temperature, in the presence of a catalyst to produce an alkoxylated product, the improvement which comprises: using as the catalyst a homogeneous catalyst composition comprising
   a. at least one ester selected from the group consisting of esters of titanic acid or zirconic acid with at least one monohydroxy alcohol having from 1 to about 4 carbon atoms, and
   b. at least one member selected from the group consisting of sulfuric acid, alkanesulfonic acids having from 1 to about 6 carbon atoms and hydroxyarylsulfonic acids.

2. A process of claim 1 wherein the amount of catalyst composition used is from about 0.1 to about 2% by weight, based on the weight of the ethoxylated product.

3. A process of claim 1 wherein the mol ratio of a. to b. is from about 1:1 to about 1:4.

* * * * *

UNITED STATES PATENT AND TRADEMARK OFFICE
CERTIFICATE OF CORRECTION

PATENT NO. : 4,983,778
DATED : January 8, 1991
INVENTOR(S) : Ploog et al.

It is certified that error appears in the above-identified patent and that said Letters Patent is hereby corrected as shown below:

In claim 1, at column 4, line 54, delete the phrase -- homogeneous catalyst --.

Signed and Sealed this

Tenth Day of August, 1993

*Attest:*

MICHAEL K. KIRK

*Attesting Officer*  *Acting Commissioner of Patents and Trademarks*